United States Patent [19]
Jankevics et al.

[11] Patent Number: 6,139,941
[45] Date of Patent: Oct. 31, 2000

[54] NONWOVEN WEB LAMINATE HAVING RELATIVELY HYDROPHILIC ZONE AND RELATED METHOD FOR ITS MANUFACTURE

[75] Inventors: Juris Jankevics, Mississauga; Glenn Roberts, Oshawa, both of Canada

[73] Assignee: BBA Nonwovens Simpsonville, Inc., Simpsonville, S.C.

[21] Appl. No.: 09/330,409

[22] Filed: Dec. 23, 1998

Related U.S. Application Data

[63] Continuation of application No. 08/878,496, Jun. 18, 1997, abandoned.
[60] Provisional application No. 60/033,253, Dec. 6, 1996.
[51] Int. Cl.$^7$ .................................. B32B 3/00; B05D 1/00
[52] U.S. Cl. ...................... 428/195; 442/382; 442/392; 442/400; 442/401; 428/198; 427/210; 427/288; 427/385.5; 427/389.9
[58] Field of Search .................................. 428/195, 198; 442/382, 392, 400, 401; 427/210, 288, 385.5, 389.9

[56] References Cited

U.S. PATENT DOCUMENTS

| | | | |
|---|---|---|---|
| 3,730,184 | 5/1973 | Mesek | 128/287 |
| 4,112,153 | 9/1978 | Butterworth et al. | 427/390 E |
| 4,298,649 | 11/1981 | Meitner | 428/198 |
| 4,328,279 | 5/1982 | Meitner et al. | 428/289 |
| 4,364,784 | 12/1982 | Van Wersch et al. | 156/78 |
| 4,384,867 | 5/1983 | Gruber | 8/477 |
| 4,436,780 | 3/1984 | Hotchkiss et al. | 428/198 |
| 4,440,838 | 4/1984 | Schmidt | 429/250 |
| 4,485,508 | 12/1984 | Otting | 8/151 |
| 4,552,778 | 11/1985 | Zimmer | 427/445 |
| 4,562,097 | 12/1985 | Walter et al. | 427/209 |
| 4,585,449 | 4/1986 | Karami | 604/378 |
| 4,620,983 | 11/1986 | Zimmer | 427/8 |
| 4,668,566 | 5/1987 | Braun | 428/286 |
| 4,753,843 | 6/1988 | Cook et al. | 428/286 |
| 4,861,652 | 8/1989 | Lippert et al. | 428/284 |
| 4,906,513 | 3/1990 | Kebbell et al. | 428/198 |
| 4,950,264 | 8/1990 | Osborn, III | 604/385.1 |
| 5,009,653 | 4/1991 | Osborn, III | 604/385.1 |
| 5,281,209 | 1/1994 | Osborn, III et al. | 604/385.1 |
| 5,330,456 | 7/1994 | Robinson | 604/368 |
| 5,486,381 | 1/1996 | Cleveland et al. | 427/294 |
| 5,527,300 | 6/1996 | Sauer | 604/378 |
| 5,562,650 | 10/1996 | Everett et al. | 604/378 |

OTHER PUBLICATIONS

Letter dated Mar. 13, 1991 from Fiberweb North America, Inc. (predecessor to BBA Nonwovens Simpsonville, Inc.) to Weyerhaeuser Corporation enclosing Celestra Unicorn spunbond zone coated product sample and specification.

*Primary Examiner*—Christopher Raimund
*Attorney, Agent, or Firm*—Ostrager Chong & Flaherty, P.C.

[57] ABSTRACT

A zone-treated spunbonded/meltblown/spunbonded (SMS) fabric laminate that combines the separate functions of the topsheet and cuff in one component of an absorbent article. The SMS fabric laminate is treated with surfactant to form a hydrophilic zone. The untreated areas of the SMS fabric laminate remain hydrophobic and perform the function of the cuff. Alternatively, a spunbonded/spunbonded fabric laminate is formed and then zone-treated with surfactant. The fabric laminate is treated with surfactant on both sides using a foam applicator. The application of foam produces sharp transitions between the hydrophilic and hydrophobic zones. After foam application, the fabric laminate is dried and slitted. The treated and slitted material is then wound and sold in roll form for converting into the finished disposable diaper.

32 Claims, 6 Drawing Sheets

NONWOVEN WEB LAMINATE HAVING RELATIVELY HYDROPHILIC ZONE AND RELATED METHOD FOR ITS MANUFACTURE

RELATED APPLICATION

This is application is a continuation of application Ser. No. 08/878,496 filed on Jun. 18, 1997 now abandoned, which claims the benefit of U.S. Provisional Application No. 60/033,253, filed on Dec. 6, 1996.

FIELD OF THE INVENTION

The invention relates to nonwoven webs suitable for use as a topsheet or body liner in a disposable diaper. In particular, the invention relates to nonwoven webs which have been treated with surfactant to increase the hydrophilicity or wettability of the fibrous material.

BACKGROUND OF THE INVENTION

Nonwoven web laminates have application in a variety of disposable products, including wipers, garments, medical drapes and absorbent articles such as diapers. One class of such nonwoven web laminates is commonly referred to as spunbonded/meltblown/spunbonded (SMS) laminates. These SMS laminates generally consist of nonwoven outer layers of spunbonded polyolefins and an interior layer of meltblown polyolefins.

As used herein, the term "nonwoven web" refers to a web that has a structure of individual fibers or filaments which are interlaid, but not in an identifiable repeating pattern.

As used herein, the term "spunbonded fibers" refers to fibers which are formed by extruding molten thermoplastic material as filaments from a plurality of fine, usually circular capillaries of a spinnerette. Cooling air is fed to a quenching chamber wherein the filaments are cooled. The cooling air is then sucked through a nozzle, which accelerates the flow of air. The friction between the flowing air and the filaments creates a force which draws the filaments, i.e., attenuates the filaments to a smaller diameter. The drawn filaments are then passed through a diffusor and deposited on a conveyor belt to form a nonwoven web. A conventional spinbonding technique is disclosed in U.S. Pat. No. 4,340,563 to Appel.

As used herein, the term "meltblown fibers" refers to fibers which are formed by extruding molten thermoplastic material as threads or filaments through a plurality of fine, usually circular capillaries of a die. A high-velocity, usually heated gas (e.g., air) stream attenuates the filaments of molten thermoplastic material to reduce their diameter. Thereafter the meltblown fibers are carried by the high-velocity heated gas stream and are deposited on a collecting surface to form a web of randomly dispersed meltblown fibers. A conventional meltblowing technique is disclosed in U.S. Pat. No. 4,707,398 to Boggs.

Meltblown fibers differ from spunbonded fibers in that the extruded polymer strands have much finer diameters. These fine diameter filaments are easily dispersed by the forced hot air stream before being deposited on the collecting surface. In addition, the meltblown fibers are substantially cooled by the air so that they do not significantly bond together. Bonding of the web to retain integrity and strength occurs as a separate downstream operation.

SMS laminates have found numerous applications. U.S. Pat. No. 4,374,888 to Bornslaeger discloses an SMS fabric suitable for use as a recreational fabric in the manufacture of tents, outer garments, tarpaulins and the like.

U.S. Pat. No. 4,766,029 to Brock discloses a house wrap consisting of an SMS laminate. The external layers are spunbonded polypropylene. The interior layer is a two-component meltblown layer of polyethylene and polypropylene. The laminate is calendared after formation so that the polyethylene melts and flows to close up the interstitial space and to bond the layers together to create a strong semi-permeable laminate.

U.S. Pat. No. 4,863,785 to Berman discloses a nonwoven composite material comprising a meltblown fabric layer of a thermoplastic polymer sandwiched between two prebonded, spunbonded reinforcing fabric layers of a thermoplastic polymer. The preferred thermoplastic polymer for both the meltblown and spunbonded layers is polypropylene.

U.S. Pat. Nos. 5,145,727 and 5,149,576 to Potts disclose a composite nonwoven including melt-extruded layers (defined as including spunbond and meltblown webs) in which fibers between the layers intermingle to form a phase boundary. The fibers of at least one of the layers is prepared by melt extrusion of a mixture of an additive and thermoplastic polymer through a die. The additive preferentially migrates to the surface of the fibers, thus imparting a selected surface characteristic to a single layer in the composite, but does not migrate to the adjoining layer. Preferred additives may impart, for example, hydrophilicity or hydrophobicity to the layer.

U.S. Pat. No. 3,730,184 to Mesek discloses a disposable diaper having a topsheet made of bonded nonwoven fabric. The mid-portion of the bonded fabric is treated with a surfactant to minimize the water repellent effect of the binder and to make the mid-portion of the fabric readily wettable. The web is impregnated with a binder fluid by flowing a solution or dispersion of the binder over the web. The central portion of the facing web is also treated with a surfactant added to the binder fluid. The binder fluid is fed to a weir box having an opening which allows the binder fluid with surfactant to pour over the central region of the web.

U.S. Pat. No. 4,112,153 to Butterworth discloses a method for controlling the water repellency in a predetermined region or zone of a nonwoven fabric. The method comprises bonding the fabric using a binder solution or suspension containing a surfactant that can be denatured or even degraded at elevated temperatures. The fabric is then subjected to a heat treatment so that in predetermined areas or regions of the fabric the surfactant that is present is denatured to provide the desired degree of hydrophobicity.

U.S. Pat. No. 4,328,279 to Meitner discloses a clean room wiper treated with surfactant. The Meitner '279 patent discloses that the surfactant can be applied by spraying, dipping, coating, impregnating or printing.

U.S. Pat. No. 4,585,449 to Karami discloses a disposable diaper having a spunbonded topsheet containing surfactant. The surfactant is applied by spraying, printing or roller coating the entire surface or in limited areas such as the central portion. Alternatively, the surfactant is line or spot printed on the topsheet to improve fluid penetration.

U.S. Pat. No. 4,950,264 to Osborn discloses a sanitary napkin having a topsheet rendered hydrophilic by treatment with surfactant. The surfactant is applied by spraying, padding or the use of transfer rolls.

U.S. Pat. No. 4,861,652 to Lippert discloses that diaper topsheets are typically composed of a liquid-permeable, substantially hydrophobic material such as a spunbonded web composed of synthetic polymer filaments.

Alternatively, the topsheet may comprise a melt-blown web or a bonded carded web composed of synthetic polymer filaments. Suitable synthetic polymers include, for example, polyethylene, polypropylene and polyesters. The topsheet must have a pore size that readily allows the passage therethrough of liquids, such as urine and other body exudates. The Lippert '652 patent also discloses that the topsheet can optionally be treated with surfactants to selectively adjust its degree of wettability.

U.S. Pat. No. 5,562,650 to Everett discloses that a diaper topsheet can be surface treated with surfactant by any conventional means, such as spraying, printing and brush coating. The surfactant material can be applied to a medial section of the topsheet layer to provide a greater wettability of the medial section, as compared to a remainder of the topsheet layer.

U.S. Pat. No. 5,330,456 to Robinson discloses a disposable absorbent panel assembly having a topsheet made of carded, spunlaced, spunbonded or thermally bonded polypropylene or polyester nonwoven fabric. The lateral central portion of the topsheet is rendered hydrophilic by application of surfactant.

U.S. Pat. No. 5,486,381 to Cleveland discloses a continuous process for non-compressively and uniformly applying a liquid saturant, such as surfactant, throughout a permeable sheet. A laminar flowing curtain of liquid saturant is deposited on one side of the permeable sheet and a vacuum is applied to the other side to generate a substantially uniform distribution of saturant throughout the sheet.

In accordance with prior practice in the manufacture of disposable diapers, separate components are used for the hydrophilic and hydrophobic regions. For example, an absorbent article consists of a topsheet which is hydrophilic and a cuff which is hydrophobic and is attached to the topsheet. The topsheet helps in fluid transfer to the absorbent core, while the cuff prevents leakage. It is known to use spunbonded fabric in the hydrophilic regions.

SUMMARY OF THE INVENTION

The present invention is a zone-treated SMS fabric laminate that combines the separate functions of the topsheet and cuff in one component of an absorbent article. The SMS fabric laminate is treated with surfactant to form a hydrophilic zone. The untreated areas of the SMS fabric laminate remain hydrophobic and perform the function of the cuff.

In addition, the SMS fabric laminate of the invention provides improved uniformity as compared to spunbonded topsheets known in the art. The improvement in uniformity is primarily due to the meltblown layer which is composed of fine fibers. The untreated meltblown layer also acts as a barrier to fluid transport.

Although the barrier posed by the meltblown layer is useful in the hydrophobic region of a disposable diaper, a barrier effect is undesirable in the central region of the diaper overlying the absorbent core structure. This problem is solved in accordance with the present invention by treating with surfactant only those zones of the SMS fabric laminate which need to be hydrophilic. On the full-width production line, a plurality of zones of the SMS fabric laminate can be treated with surfactant, each zone forming the central region of the topsheet after the full-width fabric laminate has been slitted. The result of the present invention is a zone-treated SMS fabric laminate which is lightweight and uniform; has a sharp transition between hydrophilic and hydrophobic zones; has good strike-through and rewet properties in the hydrophilic region; and acts as a good barrier in the hydrophobic region.

In accordance with alternative preferred embodiment of the invention, a spunbonded/spunbonded fabric laminate is formed and then zone-treated with surfactant.

In accordance with the preferred method of manufacture, the fabric laminate is treated with surfactant on both sides of the laminate. Furthermore, the surfactant is applied using a foam applicator rather than conventional topical application techniques, e.g., spray, kiss and padding techniques. The application of foam produces sharp transitions between the hydrophilic and hydrophobic zones. The transition regions between zones may have a width in the range of 2–15 mm, and most preferably 3–8 mm. After foam application, the fabric laminate is dried and slitted. The treated and slitted material is then wound and sold in roll form for converting into the finished disposable diaper.

DETAILED DESCRIPTION OF THE PREFERRED EMBODIMENTS

Figure 1:
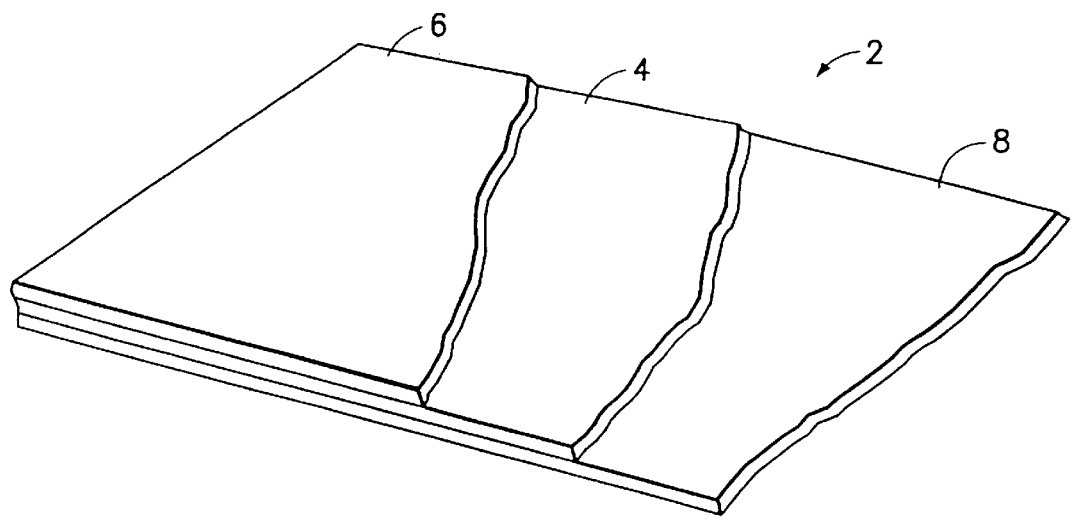
FIG. 1 is a schematic diagram showing the construction of a conventional spunbonded/meltblown/spunbonded fiber laminate.

In accordance with the present invention as illustrated in FIG. 1, a nonwoven composite material 2 is provided comprising a meltblown fabric layer 4 of thermoplastic polymeric microfibers and two spunbonded fabric layers 6 and 8 each made of thermoplastic polymer filaments.

The meltblown fabric layer 4 can be prepared by extruding a fiber-forming thermoplastic polymer resin in molten form through a plurality of fine, usually circular capillaries of a die. A high-velocity, usually heated gas (e.g., air) stream attenuates the filaments of molten thermoplastic material to reduce their diameter. Thereafter the meltblown fibers are carried by the high-velocity heated gas stream and are deposited on a collecting surface to form a nonwoven web of randomly dispersed meltblown fibers. In accordance with the preferred embodiment, the thermoplastic polymeric microfibers of meltblown fabric layer 4 are polypropylene. Polymers other than polypropylene, such as nylon, polyethylene, polyester, and copolymers and blends thereof, may also be used.

Each of the spunbonded fabric layers 6 and 8 may be produced by continuously extruding a thermoplastic polymer through a plurality of fine, usually circular capillaries of a spinnerette. Pressurized cooling air is fed to a quenching chamber wherein the filaments are cooled. The cooling air is then accelerated through a nozzle by a positive air pressure. The friction between the flowing air and the filaments creates a force which draws the filaments, i.e., attenuates the filaments to a smaller diameter. The filaments are drawn to achieve molecular orientation and tenacity. The continuous filaments are then deposited in a substantially random manner to form a web of substantially continuous and randomly arranged, molecularly oriented filaments. The preferred thermoplastic polymer used to make spunbonded fabric layers 6 and 8 is polypropylene, although nylon, polyethylene, polyester, and copolymers and blends thereof can be used.

In accordance with the conventional structure of an SMS fabric as seen in FIG. 1, the meltblown fabric layer 4 is sandwiched between the spunbonded fabric layers 6 and 8. All three of these fabric layers are then bonded together by the application of heat and pressure to form the SMS fabric laminate 2. Spunbonded fabric layers 6 and 8 are prebonded by heated press rolls providing structural integrity to the fabric.

Figure 2:
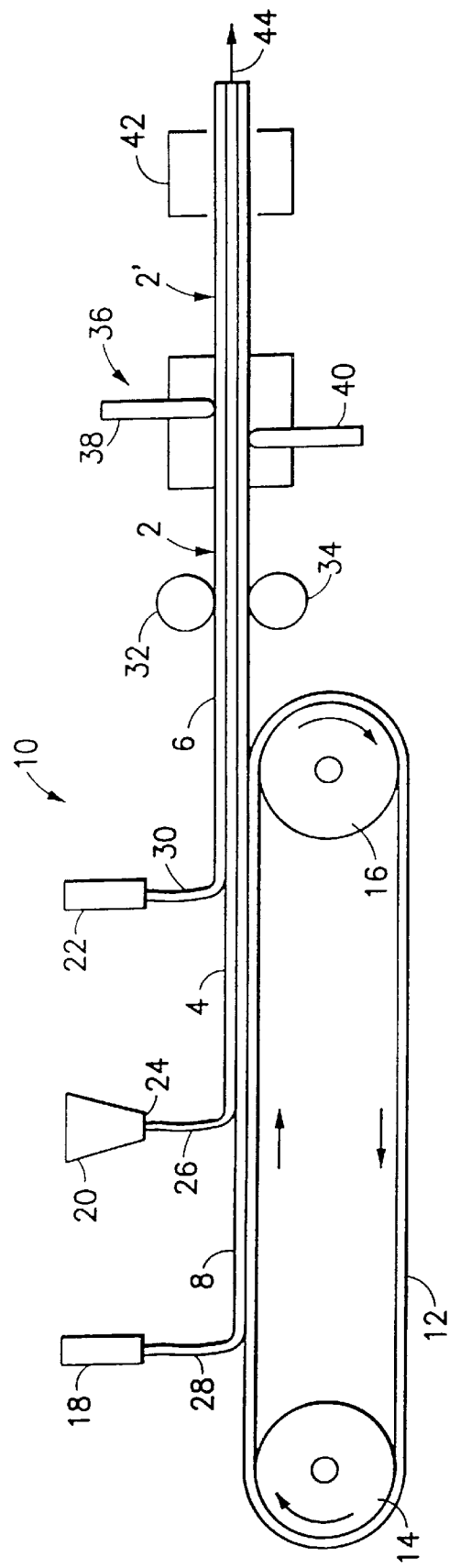
FIG. 2 is a schematic diagram showing the essential components of a system for continuously producing nonwoven web material having zones treated with an agent by foam application in accordance with the preferred embodiment of the invention.

FIG. 2 shows a production line 10 for producing an SMS fabric laminate 2 in accordance with the present invention. This production line can be operated at a speed in the range of 250 to 600 m/min, preferably about 375 m/min. The equipment of production line 10 consists of an endless foraminous forming belt 12 wrapped around rollers 14 and 16. The belt 12 is driven in the direction shown by the arrows. The production line 10 includes a forming machine which has three stations: spunbond station 18, meltblown station 20 and spunbond station 22. First, the spunbond station 18 lays down a web 8 of spunbonded fibers 28 onto the carrier belt 12. Then the meltblown station 20 lays down a web 4 of meltblown fibers 26 onto the spunbonded web 8. Lastly, the spunbond station 22 lays down a web 6 of spunbonded fibers 30 onto the meltblown web 4. Alternatively, each of the component fabric layers may be formed separately, rolled, and later converted to the SMS fabric laminate offline.

The spunbond stations 18 and 22 are conventional extruders with spinnerettes which form continuous filaments of a polymer and deposit those filaments onto the forming belt 12 in a random interlaced fashion. Each spunbond station may include one or more spinnerette heads depending on the speed of the process and the particular polymer being used. Forming spunbonded material is a conventional process well known in the art.

The meltblown station 20 consists of a die 24 which is used to form microfibers 26. As the thermoplastic polymer exits the die 24, the polymer threads are attenuated and spread by high-pressure fluid, usually air, to form microfibers 26. The microfibers 26 are randomly deposited on top of the spunbond layer 8 and form a meltblown layer 4. The construction and operation of the meltblown station 20 for forming microfibers 26 are well known in the art.

In accordance with the preferred embodiment of the invention, the meltblown fabric layer 4 has a basis weight of approximately 1.5 gsy, while the total basis weight of the spunbonded fabric layers is 10 gsy. However, in accordance with the broad concept of the invention, the basis weight of the meltblown fabric layer can be in the range of 0.5 to 6.0 gsy, while the total basis weight of the spunbonded fabric layers can be in the range of 6.0 to 20.0 gsy. Further, in accordance with the invention, the meltblown fibers have an average diameter of 1–10 $\mu$m, preferably 3–5 $\mu$m, while the spunbonded fibers have an average diameter of 10–30 $\mu$m, preferably 12–20 $\mu$m. The SMS fabric laminate in accordance with the preferred embodiment has a mean pore size in the range of 15–50 $\mu$m, preferably about 30–40 $\mu$m. The molten polypropylene used to make the meltblown fibers has a molecular weight distribution in the range of about 1.8–5.0, preferably 3.6, and a melt flow rate in the range of about 400–3000 grams/10 minutes, preferably about 1000 grams/10 minutes, whereas the molten polypropylene used to make the spunbonded fibers has a molecular weight distribution in the range of about 1.8–5.0, preferably 2.5–2.7, and a melt flow rate in the range of about 10–100 grams/10 minutes, preferably about 35 grams/10 minutes.

Out of the forming machine, the SMS fabric laminate web 2 (see FIG. 2) is then fed through bonding rolls 32 and 34. The surfaces of the bonding rolls 32 and 34 are provided with a pattern of raised lands which apply heat and pressure to thermally spot bond the three layers together. The bonding rolls are heated to a temperature which causes the meltblown polymer to soften. As the meltblown web 4 passes between the heated bonding rolls 32 and 34, the composite material is compressed and heated by the bonding rolls in accordance with the pattern on the rolls to create a pattern of discrete bonding areas. Such discrete area or spot bonding is well known in the art and can be carried out by means of heated rolls or by ultrasonic bonding. The bond pattern is selected to provide desired fabric strength characteristics. The pattern bonding area is not limited in accordance with the present invention, although pattern bonding areas in the range of 5–25%, preferably 14–19%, of the total fabric area are feasible. In the alternative, the laminate can be ultrasonically spot bonded or bonded by hot melt/glue adhesive lamination.

In accordance with a second preferred embodiment of the invention, a spunbonded/spunbonded (SS) fabric laminate is formed by operating only spunbond stations 18 and 22, i.e., meltblown station 20 is turned off. In this case, the bonding rolls 32 and 34 must be heated to a temperature which causes the spunbonded polymer to soften. The SS fabric laminate will have the same tensile strength and elongation as an SMS fabric laminate having the same spunbonded layers since the meltblown layer does not contribute to these physical properties.

The precursor SMS (or SS) fabric laminate exiting the bonding station is inherently hydrophobic. In accordance with the present invention, certain regions of the hydrophobic fabric laminate are rendered hydrophilic by zone treatment with surfactant. As used herein, the term "zone treatment" refers to the application of an agent to a nonwoven fabric in one or more zones of the fabric, while the remainder of the nonwoven fabric is untreated.

Referring to FIG. 2, the SMS fabric laminate 2 is passed through a foam applicator 36 which treats both sides of the SMS (or SS) fabric laminate with surfactant. The foam applicator 36 comprises an upper parabolic foam distribution chamber 38 and a lower parabolic foam distribution chamber 40. The upper parabolic foam distribution chamber 38 applies surfactant to the top surface of the SMS (or SS) fabric laminate, whereas the lower parabolic foam distribution chamber 40 applies surfactant to the bottom surface of the fabric laminate. The amount of surfactant applied on each side must be sufficient to ensure that, not only the fibers of the spunbonded fabric layers 6 and 8, but also the fibers of the meltblown fabric layer 4 are coated with surfactant as a result of the treatment. The surfactant increases the wettability of the polymeric fibers in those zones of the laminate on which surfactant is applied.

The preferred surfactant is an anionic surfactant which lowers the surface tension of water/urine. The surfactant used was Triton X-200 supplied by Union Carbide. Triton X-200 is a viscous, milky white, aqueous dispersion having good detergency and foaming properties. The active component of Triton X-200 is the sodium salt of an alkylaryl polyether sulfonate. However, the present invention is not limited to the use of a particular surfactant. Any agent in liquid form which has the property of increasing the wettability of polymeric fibers can be used. Other surfactants which may be used include Nu Wet supplied by Organic Solutions Inc. and BK2105 surfactant made by Henkel, Dusseldorf, Germany.

The foam applicator 36 is designed to apply surfactant-containing foam to the SMS fabric laminate in predetermined zones only as the bonded fabric laminate is advanced in the direction indicated by arrow 44 in FIG. 2. The use of foam as the application medium allows the location of the surfactant on the fabric laminate to be precisely controlled. Immediately after exiting the foam applicator, the treated fabric laminate 2' is exposed to heat in a dryer 42, e.g., a through-air oven heated to a temperature of 120° C. The application of heat to the treated fabric laminate causes the water to be evaporated and the surfactant to be impregnated within the fibers before the surfactant has had time to migrate laterally to any significant extent.

Figure 6:
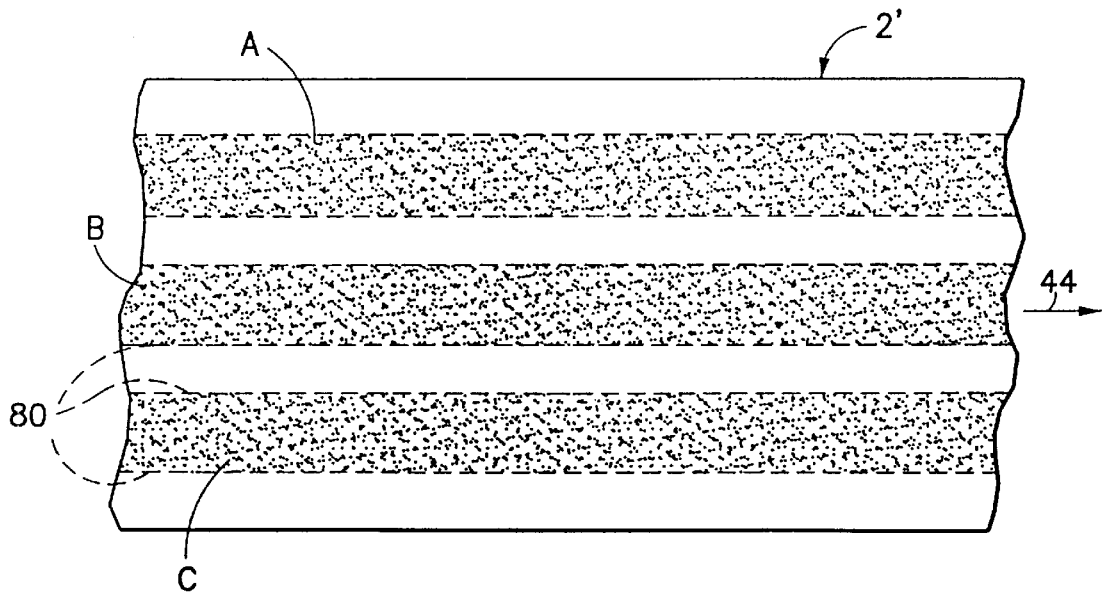
FIG. 6 is a schematic diagram showing the zonal treatment of a spunbonded/meltblown/spunbonded fiber laminate in accordance with the preferred embodiment of the invention.

The result is a zone-treated SMS (or SS) fabric laminate in which each demarcation between a hydrophilic zone and each adjacent hydrophobic zone is sharp and precisely located. For example, FIG. 6 shows a fabric laminate made of hydrophobic polymeric material, e.g., polypropylene, which has been treated with surfactant in accordance with the present invention to provide three hydrophilic zones A, B and C. Treatment with surfactant is indicated by shading in FIG. 6, whereas the unshaded areas indicate the remaining hydrophobic zones which have not been treated with surfactant. The surfactant is applied at a fixed location along the production line while the fabric laminate is being advanced in the machine direction indicated by arrow 44.

Dotted lines 80 between adjacent hydrophilic and hydrophobic zones represent the sharp transition regions. The width of each transition region is preferably 2–15 mm, and most preferably 2–8 mm. The width is tested by applying drops of water or synthetic urine in several lines across the width of the fabric (i.e., in the cross direction). The drops will bead up in the hydrophobic zones and will seep through the hydrophilic zones A, B, C. The width of the line of beaded drops formed in the machine direction is then measured.

In one example of the zone-coated SMS fabric in accordance with the invention, the transition region had a width of 2 mm. The test fabric of this example was an 11.5 gsy SMS fabric comprising two spunbond layers having a total weight of 10 gsy and a meltblown layer having a weight of 1.5 gsy. The fabric was 50% zone-coated under the following parabolic foam distribution chamber conditions: liquid flow of 2.65 liters/min; surfactant flow of 0.1 liter/min; mix air blow ratio of 80:1; and line speed of 250 m/min. Strike-through, rewet and penetration properties were then tested over several trial runs. The fabric exhibited an average

TABLE 1

| Run | Strike-through (sec) | Rewet (gm) |
| --- | --- | --- |
| 1 | 1.55 | 1.03 |
| 2 | 1.64 | 1.31 |
| 3 | 1.78 | 0.50 |
| 4 | 1.68 | 1.15 |
| 5 | 1.70 | 1.28 |
| 6 | 1.99 | 1.10 |
| 7 | 1.69 | 0.38 |
| 8 | 1.80 | 1.40 |
| 9 | 1.77 | 1.48 |
| 10 | 1.93 | 1.22 |
| 11 | 1.81 | 1.32 |
| 12 | 1.77 | 1.60 |
| Average | 1.76 | 1.15 |
| Std. Dev. | 0.12 | 0.35 | strike-through of 1.76 seconds, rewet of 1.15 grams and 82% penetration. Table 1 shows the results of each trial run.

Figure 5A:
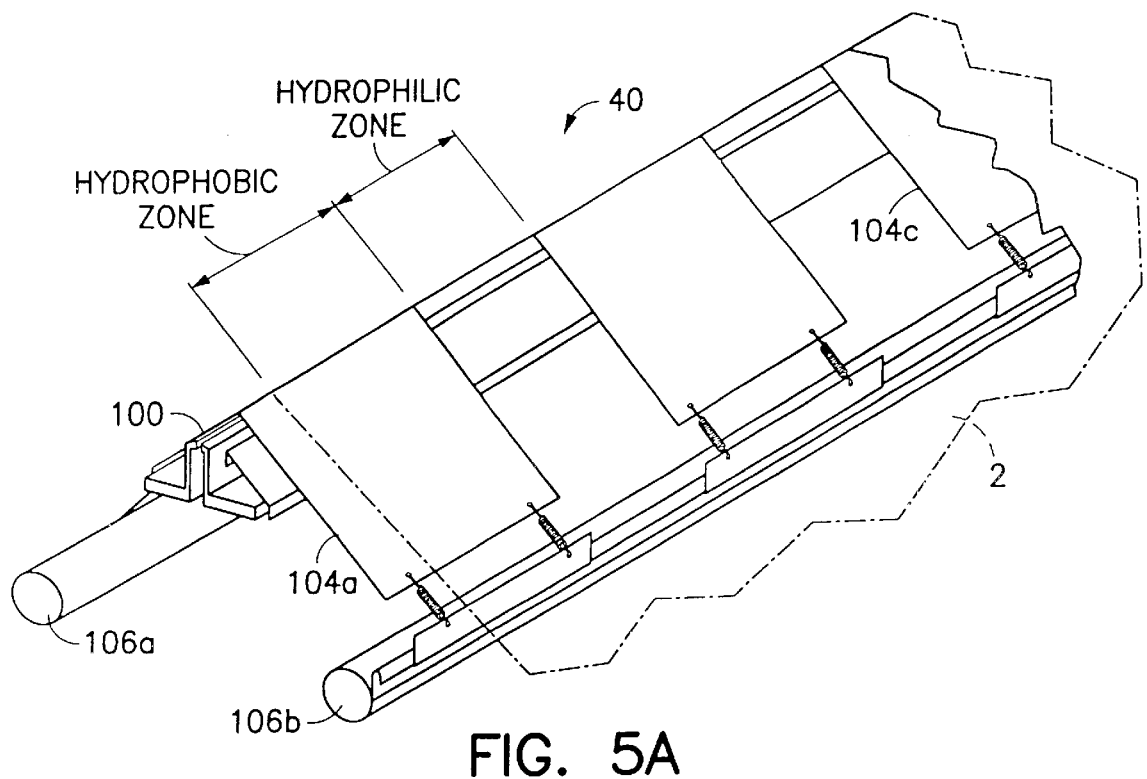
FIG. 5A is a schematic diagram showing a lower parabolic foam distribution chamber retrofitted with shim plates in accordance with the preferred embodiment of the invention.
Figure 5B:
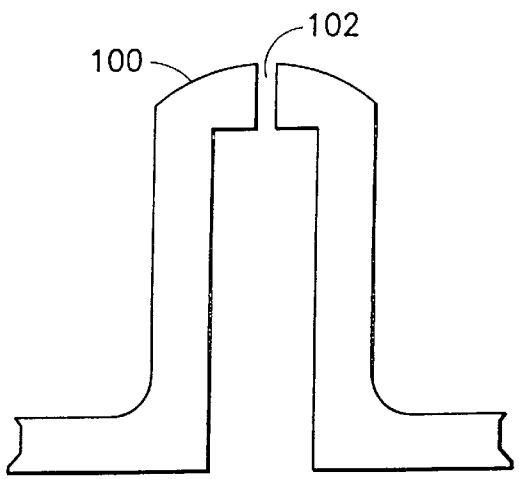
FIG. 5B is a schematic diagram showing an end view of the lip of the parabolic foam distribution chamber of FIG. 5A.

A lower parabolic foam distribution chamber of the foam applicator in accordance with the present invention is shown in FIG. 5A. Parabolic foam distribution chambers are commercially available from Gaston County Dyeing Machine Company, Stanley, N.C. The distribution chamber includes a lip 100 having a slot 102 (shown in greater detail in FIG. 5B) from which surfactant foam exits and contacts the fabric laminate 2 (indicated by the dash-dot line in FIG. 5A). The slot 102 has a width of approximately 1 inch.

The slotted lip 100 has one or more sections closed off to prevent surfactant foam from being applied to the fabric laminate in a zone coextensive with the closure length. The slot in lip 100 is partially closed by a plurality of shim plates 104a, 104b, 104c, etc., spaced along the length of the slot with gaps therebetween. These gaps, which allow the foam to exit the foam distribution chamber via the slot, define the zones to be treated with surfactant as the fabric laminate is continuously advanced across the slotted lip 100. The fabric laminate 2 being advanced across lip 100 is impregnated with foam only in the zones where foam is escaping from the slot-like opening, e.g., zones A, B and C seen in FIG. 6. The shim plates 104a, 104b, 104c, etc. have one end attached to a mounting bar 106a, an intermediate portion partially wrapped around the lip 100, and another end attached to a tensioning bar 106b via springs for adjusting the tension in the shim plates. Because lip 100 is linear, the fabric laminate being passed across the slot 102 remains substantially flat.

Figure 3:
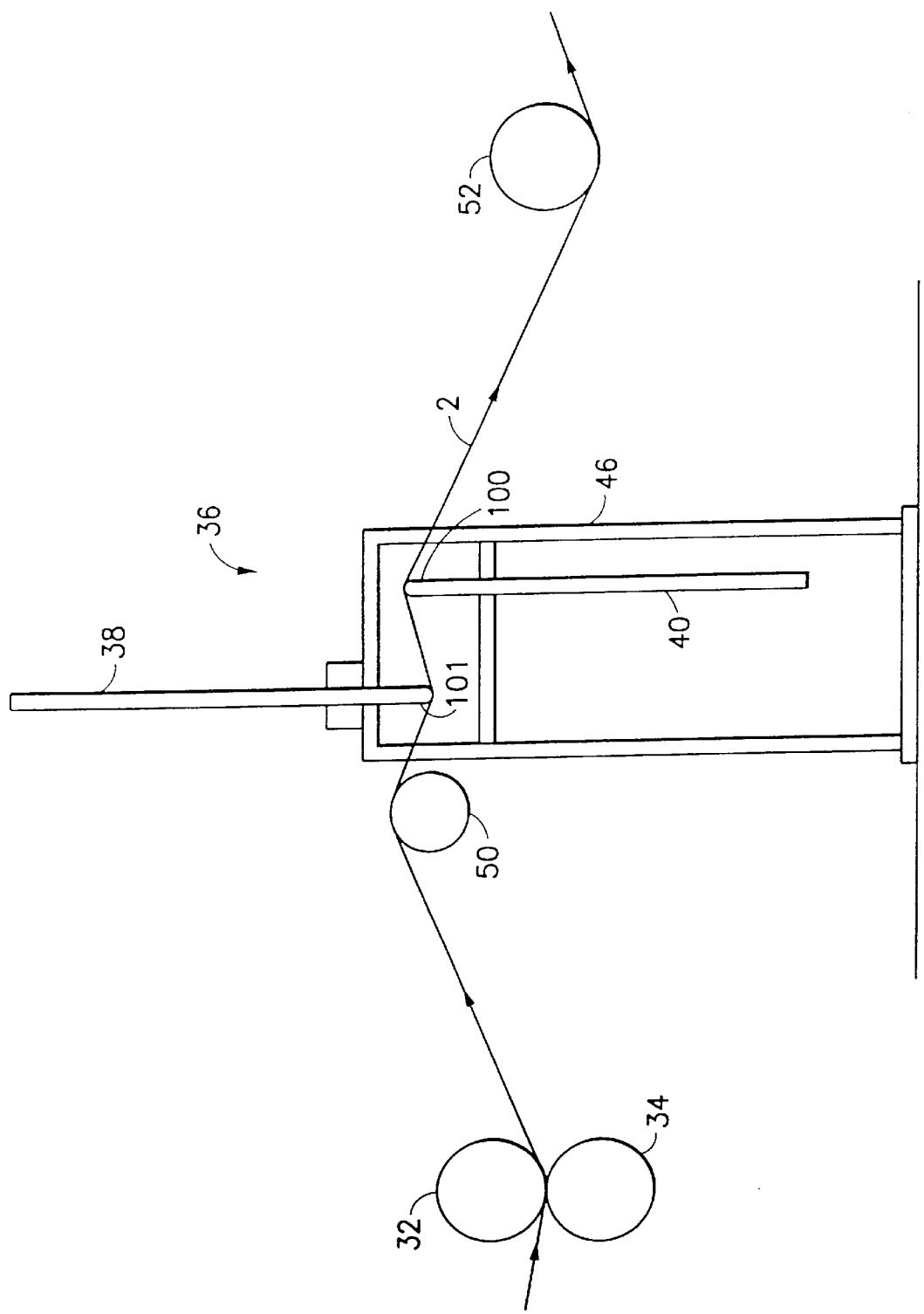
FIG. 3 is a schematic diagram showing a foam applicator and associated rolls incorporated in the system shown in FIG. 2.

The structure of the foam applicator 36 is shown in FIG. 3. The applicator comprises a frame 46 which supports an upper parabolic foam distribution chamber 38 and a lower parabolic foam distribution chamber 40 in generally vertical positions as shown. The SMS fabric laminate 2 exits the bonding rolls 32, 34 and is guided into the foam applicator 36 by guide roll 50. The uppermost point on guide roll 50 is at an elevation above the elevation of the lip 101 of upper parabolic foam distribution chamber 38. The fabric laminate 2 is passed under the lip 101 and then over the lip 100—which lies at an elevation higher than the elevation of lip 101—of lower parabolic foam distribution chamber 40. After exiting the foam applicator 36, the continuously advancing fabric laminate wraps partially around a dryer intake roll 52, which forms part of a through-air (Fleissner) dryer.

The topside of the continuously advancing fabric laminate 2 is impregnated with foam in those sections of lip 101 in which the slot-like opening is not closed by shim plates. The foam application onto the continuously advancing fabric laminate creates surfactant-treated zones (see zones A, B and C in FIG. 6) which run parallel to the machine direction. Thereafter the underside of fabric laminate 2 is impregnated with foam in the same foam impregnation zones by corresponding sections of lip 100 in which the slot-like opening is not closed by shim plates. The result is a fabric laminate in which the layers, including the central meltblown layer, are thoroughly coated with surfactant in the treatment zones and thus rendered hydrophilic.

Figure 4:
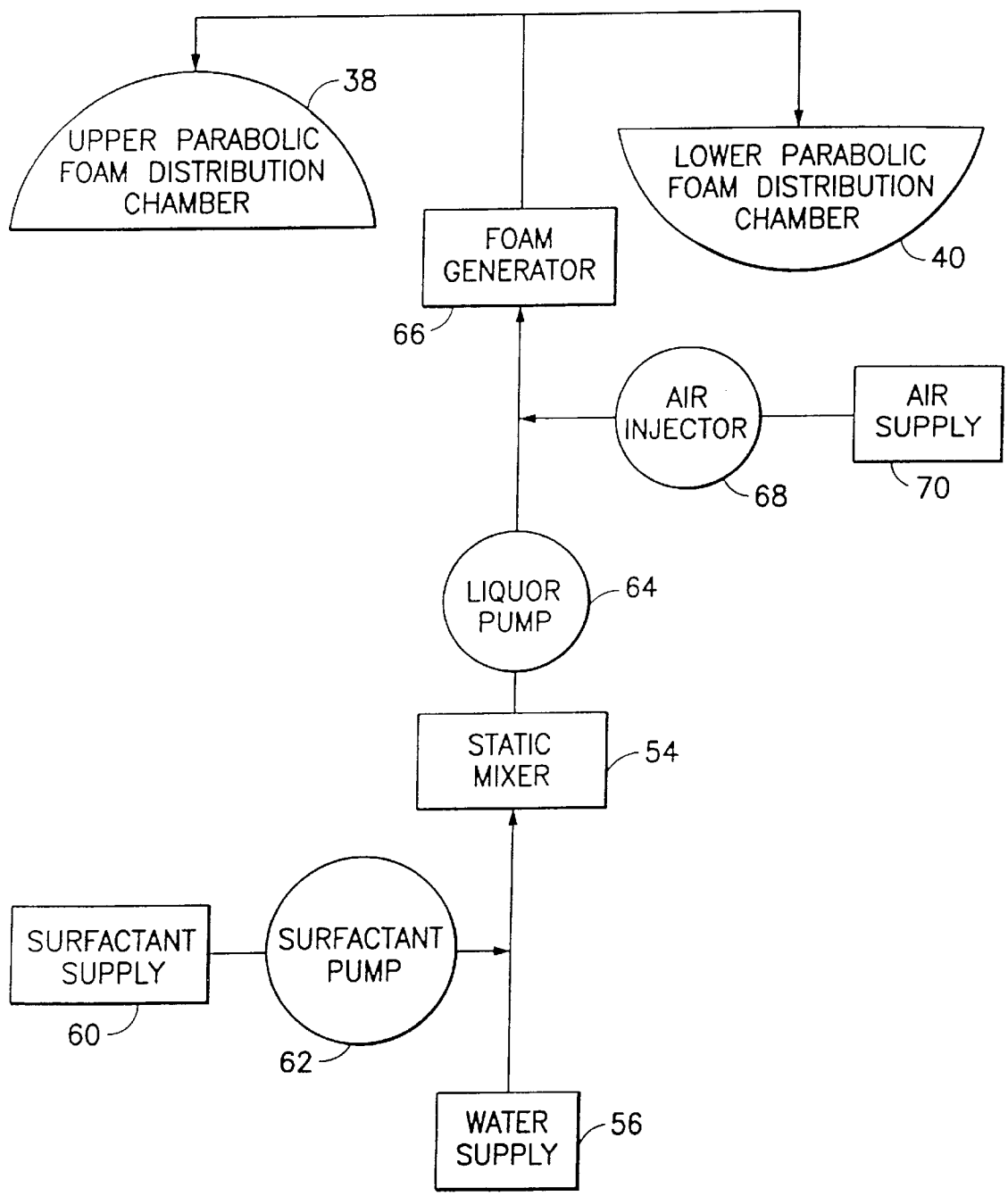
FIG. 4 is a flow diagram showing the process flow for generation and distribution of foam in the foam applicator system in accordance with the preferred embodiment of the invention.

The foam distribution system, generally depicted in FIG. 4, comprises a static mixer 54 having an inlet for receiving soft water from a water supply 56 and surfactant in liquid form from a surfactant supply. The surfactant-to-water ratio is typically approximately equal to 10, although the present invention is not limited to a particular surfactant-to-water ratio. The surfactant is metered through a pump 62 into a stream of soft water. The combination of surfactant and soft water is hereinafter referred to as "liquor". The liquor is mixed by the static mixer 54 and thereafter a stream of liquor is pumped through the liquor pump 64 to a foam generator 66. Just prior to entering the foam generator 66, the liquor stream is injected 68 with a predetermined volume of air 70. Pumps 64 and 68 are controlled by a pump control system (not shown). The blow ratio (i.e., the volume ratio of air to liquid) for the fluids injected into foam generator 66 is typically equal to 80, although the present invention is not limited to a particular air-to-liquid ratio. The foam generator 66 is a conventional device which continuously produces foam by way of air being injected into the liquor solution. The foam is continuously pumped out of the foam generator 66 to the parabolic foam distribution chambers 38, 40 by way of two separate lines. Preferably, the foam density is 0.028 to 0.034 gm/cc; the average bubble diameter is 0.1 to 0.3 mm; the foam half-life is 7 to 10 minutes; and the foam traveling time is 0.22 to 0.28 minutes.

As seen in FIG. 4, each parabolic foam distribution chamber has a predetermined shape with a parabolic boundary and a linear or straight boundary. The chamber consists of two congruent parallel plates having the predetermined shape and a parabolic wall which closes the parabolic periphery. The linear boundary is open to form a slot-like outlet for the foam. As previously described, each parabolic foam distribution chamber has an inlet for foam situated at the focal point of the parabola. This ensures that all of the foam travels the same distance, thereby preventing nonuniform degradation of the foam with the lapse of time. Such parabolic foam distribution chambers are commercially available. In the commercially available device, the parabolic foam distribution chamber ensures uniform foam distribution across the full applicator slot width. The applicator is provided with an air-inflated slot bladder (not shown in FIG. 5B) which extends across the full width of the applicator inside the lip 100. The slot bladder closes the applicator slot 102 when inflated to prevent surfactant foam from exiting the lip 100. Also, foam slot end seals (not shown) are provided which block off each end of the foam slot 102 not covered by the fabric laminate being treated.

As used herein, the term "strike-through" means the time required for a given volume of surface-applied synthetic urine to enter or "strike-through" a nonwoven sheet into an absorbent structure; and the term "rewet" means the amount of liquid which flows back through the top sheet under loading pressure to cause wetness at the original liquid entry surface. The term "rewet" is also known as "surface dryness".

The test procedure for determining strike-through and rewet is generally described as follows. The test solution is applied to an absorbent structure simulating a diaper. The time required for a specific volume of liquid to enter the absorbent structure, i.e., the strike-through value, is accurately measured and expressed in seconds. After the strike-through has been measured, an additional quantity of liquid is applied to bring the total liquid application to some desired loading multiple of the absorbent structure weight. When the total value of liquid has been applied, it is allowed to distribute through the absorbent structure, under a loading pressure, for an equilibration period. Following this period, dry absorbent paper is placed under the loading weight and is allowed to absorb moisture during a second equilibration period. The gain in weight of the absorbent paper, i.e., rewet, is reported in grams. Increasing rewet numbers indicate poorer dryness performance. The test is run at laboratory conditions of 73° F.±2° F. and 50%±2% relative humidity.

The following apparatus and materials are required to carry out the foregoing test procedure:

(1) An electrical ON/OFF timer accurate to 0.01 sec digital lab timer.

(2) A strike-through test plate consisting of a 4"×4" plastic plate with a centered patterned hole layout for distributing the liquid.

(3) A test solution of synthetic urine, e.g., 110.4 gm of syn-Urine (commercially available from Jayco Pharmaceuticals, Mechanicsburg, Pa. 17055) dissolved in 20,000 ml of distilled water.

(4) A 50-ml automatic burette with a 1000-ml dispensing bottle.

(5) A 125-ml globe-shaped separating funnel with a Teflon stopcock which will allow a discharge rate of 25 ml in 3.5±0.25 sec. The stem of the funnel must be cut off at a right angle about 1" below the stopcock.

(6) A ring stand and burette clamps.

(7) One 5"×5"×¼" Plexiglass base plate for each test setup.

(8) A pressure plate consisting of a soft foam pad 4"×4"×5" backed with a stiffening plastic or metal 4"×4" plate and the entire assembly wrapped in a 0.003" water-impervious polyethylene sheet. The entire plate weighs approximately 8 lbs. One pressure plate is needed for each test setup.

(9) A 5"×5" die to cut samples.

(10) Eaton-Dikeman 3.8 loading core material.

(11) An analytical balance accurate to 0.001 gm.

(12) Eaton-Dikeman filter paper No. 631 (5"×5" squares).

(13) A 60-min timer with a sweep second hand and stop/reset buttons.

The test procedures will now be described in detail.

(1) Three sections of the Eaton-Dikeman 3.8 loading make up one test core pad. Weigh each sample to the nearest 0.01 gm. The weight of the pad must be within the specified range on the factor table. Cores must be conditioned for at least 24 hr at 73° F. and 50% relative humidity.

(2) Die cut a 5"×5" square sample of topsheet material. Weigh and record the topsheet sample to 0.01 gm. If the sample is outside of the weight specification, discard it.

(3) Measure and record the sample thickness.

(4) Weigh two Eaton-Dikeman No. 631 filter papers and record the weight in the records to the nearest 0.01-gm. Filter papers must be conditioned for a minimum of 2 hr at 73° F. and 50% relative humidity.

(5) Place the absorbent core structure on a dry 5"×5"×¼" Plexiglass plate. Place a previously cut and weighed 5"×5" topsheet sample over the absorbent core, centering it. Center the entire assembly under the dropping funnel stem with the tip of the funnel 1⅛"±1/32" above the top of the Plexiglass plate. [Note: The bottom of the strike-through plate cavity between the electrode points must be cleaned with a mild soap solution and a pipe cleaner.]

(6) Fill the 50-ml burette to the top zero graduation with synthetic test solution. With the separating funnel stopcock closed, discharge 5 ml of solution from the burette into the funnel.

(7) With the timer power on, the timer set to zero and the wires connected to the strike-through plate, start the test by opening the funnel stopcock and discharging the 5 ml of solution into the strike-through plate cavity. Record the strike-through time after the liquid has emptied from the cavity. After the timer has shut off, discharge from the burette, into the closed funnel, the remaining amount of test solution required to bring the total test solution level to the desired pad multiple (3.8) loading factor.

(8) Immediately following completion of the pad loading, quickly remove the assembly from under the burette and the strike-through plate from the top of the sample and start the timer. Care should be taken so that the pressure plate is positioned gently and not dropped or placed with excessive pressure on the test sample. [Note: Care must be taken to position the 8-pound weight slowly and gently on the sample over a 5-sec time span.]

(9) When the timer shows an elapsed time of exactly 3 min, stop the timer, quickly remove the pressure plate, wipe the pressure plate dry, center two preweighed filter papers over the sample assembly, start the timer. The elapsed time for absorption by the filter paper is 2 min.

(10) Following the final 2-min equilibration period, the filter paper is removed weighed and the weight is recorded. The rewet is equal to the difference in weight (in grams) between the wet filter and the dry filter.

Three strike-throughs were completed on each roll to be tested, the average of the three strike-throughs was recorded. Similarly, three rewets were completed for each roll to be tested, the average of the three rewets being recorded.

Trials were run to produce SMS fabrics of different basis weights as well as a spunbonded/spunbonded (SS) laminate to evaluate the effect of lower surfactant add-on level and lower meltblown (MB) layer basis weight on liquid transfer properties such as strike-through time, rewet, etc. The first objective of the trials was to evaluate the effect of lowering the basis weight of the meltblown layer and lowering the surfactant add-on level on: (a) strike-through time; (b) rewet; (c) air permeability; and (d) tensile strength. The second objective of the trials was to assess the suitability of employing SMS fabrics with lower meltblown layer basis weight of SS fabrics as topsheet material in a disposable diaper. The trial matrix was designed as shown in Table 2.

TABLE 2

| Run | SS Weight (gsm) | MB Weight (gsm) | Surfactant Load (liter/min) | Water Load (liter/min) |
|---|---|---|---|---|
| 1 | 12.0 | 1.8 | 0.2 | 2.0 |
| 2 | 12.0 | 1.8 | 0.3 | 3.0 |
| 3 | 12.6 | 1.2 | 0.2 | 2.0 |
| 4 | 12.6 | 1.2 | 0.3 | 3.0 |
| 5 | 13.4 | 0.4 | 0.2 | 2.0 |
| 6 | 13.4 | 0.4 | 0.3 | 3.0 |
| 7 | 13.8 | 0 | 0.2 | 2.0 |
| 8 | 13.8 | 0 | 0.3 | 3.0 |

The trials were run at the following conditions: line speed, 375 m/min; blow ratio, 40–100; wet pick-up, 5–20%; surfactant/water ratio, 2–15%. The surfactant was Triton X-200 supplied by Union Carbide.

During the experiments, the hydrohead pressure at the top and bottom parabolic applicators was observed to be increased with surfactant add-on rate as follows: ~3.5 inches of water at a surfactant add-on rate of 0.2 liter/min and ~5.0 inches of water at 0.3 liter/min. A higher surfactant add-on rate contributes to higher blow volume of air at a constant blow ratio (80) on the applicator head and a higher blow volume of air would create higher pressure at the applicator head. Furthermore, buildup of the surfactant on the parabolic heads decreased with lower meltblown layer basis weight. Lower buildup of the surfactant contributes to higher permeability of the web and/or lower head pressure. Also the cut width at the slitting station decreased with lower meltblown layer basis weight, where the improved CD strength mainly from the meltblown layer could be a major factor contributing to cut width stability.

Thirteen or 14 samples from the parent roll of each run were tested for strike-through time and rewet and 5 samples were tested for air permeability and tensile strength. The testing results of the samples from Runs 1 to 8 are summarized in Table 3 and the strike-through time and rewet of the 13 or 14 samples from Runs 1 to 8 are listed in Table 4. The dependence of the strike-through time and rewet on meltblown layer basis weight is shown respectively in FIGS. 7 and 8.

Figure 7:
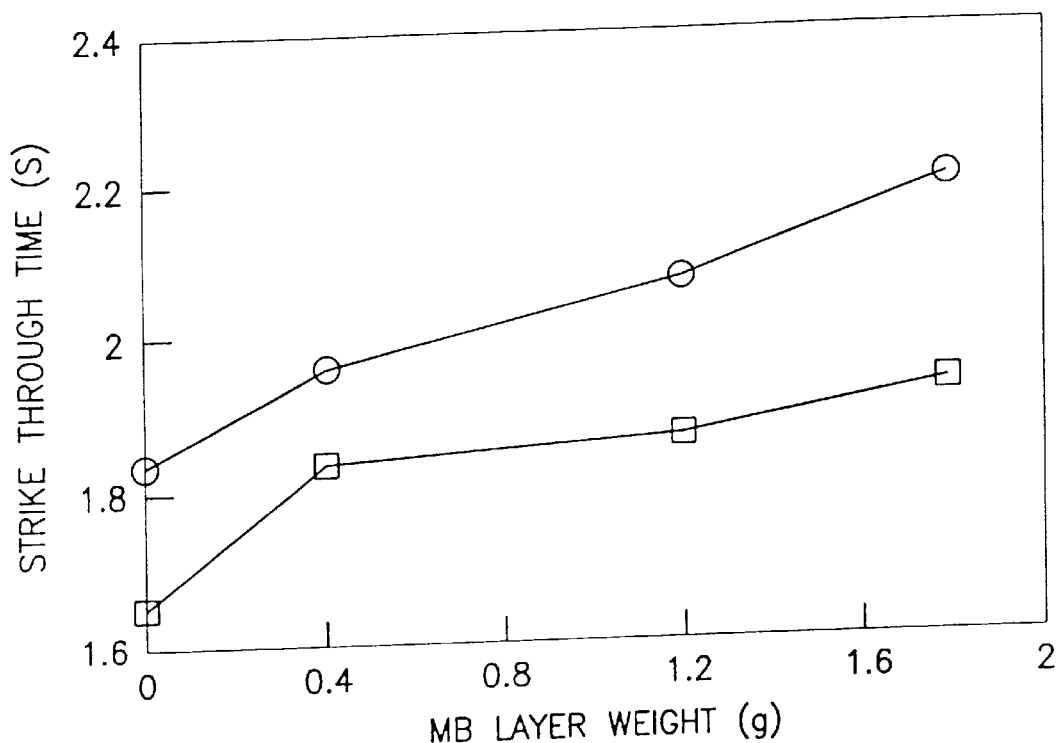
FIG. 7 is a graph showing the strike-through time (sec) of an SMS laminate versus the basis weight (gsm) of the meltblown layer at different surfactant add-on rates (liters/min): (○) 0.2; (□) 0.3.

As shown in FIG. 7, the strike-through time decreased with decreasing meltblown layer basis weight, but not as significantly as expected. The strike-through time improved (decreased) 16.8% when the melt-blown layer weight was lowered 100%, i.e., from 1.8 gsm to 0 at a surfactant add-on rate of 0.2 liter/min; and only 14.5% at the rate of 0.3 liter/min. This indicates that at a lower surfactant add-on rate, the strike-through time can be slightly more significantly affected by changing meltblown layer basis weight. Also the strike-through time was consistently improved (decreased) with increasing surfactant add-on level, but not significantly.

TABLE 3

|  | Run 1 | Run 2 | Run 3 | ROLL 4 | Run 5 | Run 6 | Run 7 | Run 8 | Carded Web |
|---|---|---|---|---|---|---|---|---|---|
| BASIS WEIGHT GSM | 14.1 | 14.1 | 14 | 14.1 | 14.2 | 14 | 13.8 | 13.8 | 19.1 |
| CD TENSILE G/IN | 784 | 1025 | 841 | 910 | 618 | 581 | 632 | 739 | 300 |
| CD ELONG. % | 65 | 68 | 62 | 40 | 63 | 62 | 56 | 64 | 88 |
| MD TENSILE G/IN | 1695 | 1667 | 1815 | 1387 | 1430 | 1668 | 1293 | 1424 | 1300 |
| MD ELONG. % | 54 | 52 | 52 | 45 | 52 | 40 | 55 | 47 |  |

TABLE 3-continued

|  | Run 1 | Run 2 | Run 3 | ROLL 4 | Run 5 | Run 6 | Run 7 | Run 8 | Carded Web |
|---|---|---|---|---|---|---|---|---|---|
| STRIKE THROUGH SEC | 2.2 | 1.93 | 2.06 | 1.86 | 1.95 | 1.83 | 1.83 | 1.65 | 1.9 |
| REWET GRS | 0.14 | 0.18 | 0.16 | 0.19 | 0.19 | 0.21 | 0.11 | 0.23 | 0.09 |
| PERMEABILITY CFM | 392 | 403 | 422 | 4.2 | 567 | 537 |  |  |  |
| MB GSM | 1.8 | 1.8 | 1.2 | 1.2 | 0.4 | 0.4 | 0 | 0 |  |
| CHEMICAL | 0.199 | 0.301 | 0.204 | 0.301 | 0.291 | 0.299 | 0.2 | 0.3 |  |
| WATER | 0.1994 | 2.984 | 1.961 | 3.025 | 1.889 | 3.006 | 2 | 3 |  |
| PENETRATION % | 18.1 | 48.8 | 27.65 | 53.86 | 53.64 | 52.31 | 79 | 89 |  |

TABLE 4

| Duplicate | 1 | 2 | 3 | 4 | 5 | 6 | 7 | 8 | 9 | 10 | 11 | 12 | 13 | 14 | Average | STDS |
|---|---|---|---|---|---|---|---|---|---|---|---|---|---|---|---|---|
| STRIKETRHOUGH | | | | | | | | | | | | | | | | |
| Run 1 | 2.25 | 2.29 | 2.17 | 1.72 | 2.29 | 2.34 | 2.18 | 2.35 | 2.21 | 1.9 | 2.14 | 2.04 |  | 2.52 | 2.2 | 0.14 |
| Run 2 | 2.13 | 1.89 | 2.01 | 1.96 | 1.8 | 1.92 | 1.96 | 1.84 | 1.98 | 1.56 | 1.8 | 1.9 | 1.73 | 2.18 | 1.93 | 0.13 |
| Run 3 | 2.2 | 2.2 | 2.05 | 1.78 | 2.07 | 2.25 | 2.05 | 2.02 | 1.75 | 2.34 | 2.26 | 1.7 |  |  | 2.06 | 0.21 |
| Run 4 | 2.13 | 1.77 | 2.07 | 1.78 | 1.9 | 1.7 | 1.84 | 1.62 | 1.95 | 1.75 | 1.84 | 1.89 | 1.74 |  | 1.86 | 0.13 |
| Run 5 | 1.96 | 1.75 | 2.24 | 1.98 | 2.3 | 2 | 1.86 | 2.02 | 2.47 | 2.39 | 2.6 | 1.66 | 2.06 |  | 1.95 | 0.11 |
| Run 6 | 1.98 | 1.92 | 1.9 | 1.98 | 1.93 | 2.3 | 1.78 | 1.79 | 1.76 | 1.61 | 2.25 | 1.63 | 1.91 | 2.01 | 1.83 | 0.13 |
| Run 7 | 1.75 | 1.89 | 1.83 | 1.91 | 1.68 | 1.82 | 1.96 | 1.77 | 2.01 | 1.74 | 1.84 | 1.8 | 1.81 |  | 1.65 | 0.12 |
| Run 8 | 1.82 | 1.47 | 1.67 | 1.82 | 1.67 | 1.63 | 1.6 | 1.44 | 1.69 | 1.7 | 1.68 | 1.7 | 1.5 |  | 1.83 | 0.09 |
| REWET | | | | | | | | | | | | | | | | |
| Run 1 | 0.09 | 0.09 | 0.1 | 0.15 | 0.12 | 0.2 | 0.14 | 0.16 | 0.18 | 0.18 | 0.44 | 0.14 |  | 0.18 | 0.14 | 0.04 |
| Run 2 | 0.24 | 0.11 | 0.14 | 0.08 | 0.1 | 0.27 | 0.23 | 0.18 | 0.28 | 0.56 | 0.12 | 0.21 | 0.12 | 0.21 | 0.18 | 0.07 |
| Run 3 | 0.17 | 0.14 | 0.15 | 0.18 | 0.15 | 0.82 | 0.12 | 0.12 | 0.15 | 0.22 | 0.21 | 0.13 |  |  | 0.16 | 0.03 |
| Run 4 | 0.33 | 0.49 | 0.12 | 0.17 | 0.16 | 0.16 | 0.26 | 0.21 | 0.24 | 0.18 | 0.17 | 0.24 | 0.17 |  | 0.19 | 0.04 |
| Run 5 | 0.86 | 0.51 | 0.31 | 0.19 | 0.21 | 0.16 | 0.14 | 0.39 | 0.07 | 0.14 | 0.24 | 0.14 | 0.17 |  | 0.18 | 0.07 |
| Run 6 | 0.11 | 0.21 | 0.22 | 0.38 | 0.22 | 0.51 | 0.2 | 0.12 | 0.17 | 0.14 | 0.38 | 0.49 | 0.15 | 0.15 | 0.2 | 0.09 |
| Run 7 | 0.11 | 0.09 | 0.11 | 0.1 | 0.11 | 0.04 | 0.09 | 0.1 | 0.11 | 0.11 | 0.15 | 0.07 | 0.04 |  | 0.11 | 0.02 |
| Run 8 | 0.24 | 0.16 | 0.41 | 0.65 | 0.63 | 0.2 | 0.11 | 0.11 | 0.67 | 0.62 | 0.51 | 0.4 | 0.5 |  | 0.23 | 0.12 |

Figure 8:
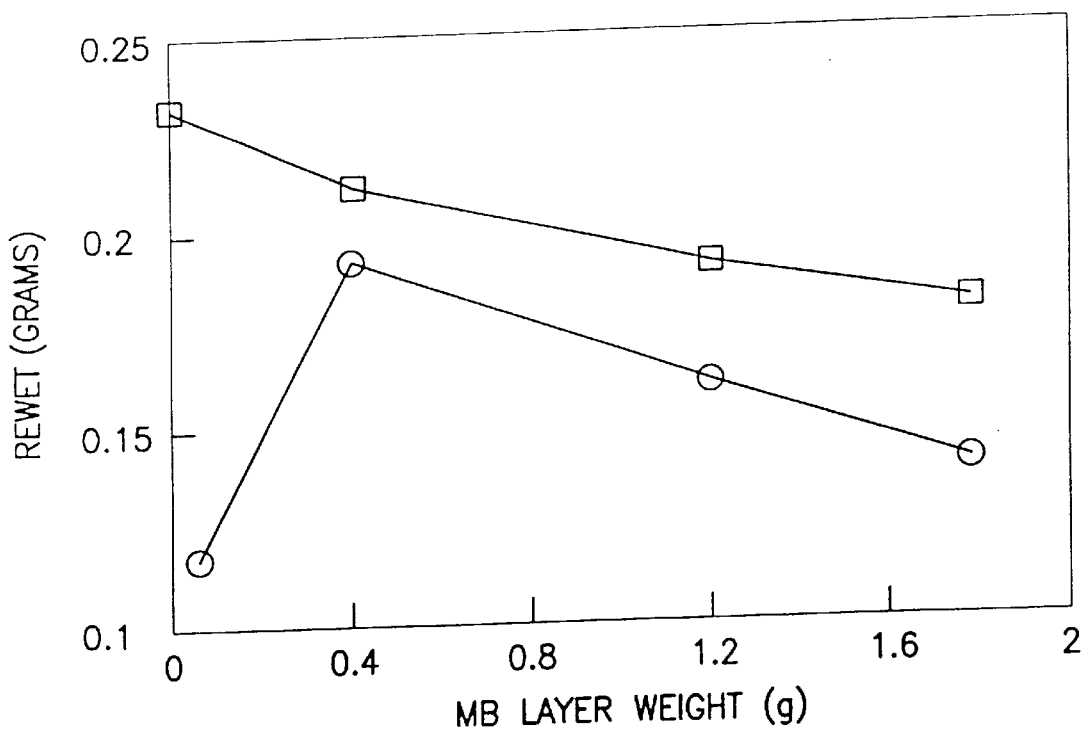
FIG. 8 is a graph showing the rewet (gm) of an SMS laminate versus the basis weight (gsm) of the meltblown layer at different surfactant add-on rates (liters/min): (○) 0.2; (□) 0.3.

The dependence of rewet on meltblown layer basis weights at different surfactant add-on rates is shown in FIG. 8. Rewet consistently decreases with increasing meltblown layer basis weight. Rewet for the SS fabric (with zero meltblown layer basis weight) at the surfactant add-on rate of 0.2 liter/min was abnormally low and could be a testing error considering a large spread of the rewet data shown in Table 4. Meanwhile rewet decreases with decreasing surfactant add-on rate. The data listed in Table 3 demonstrate that both CD and MD tensile strength have no obvious correlation with melt-blown layer basis weight and surfactant add-on level and that the air permeability consistently increases with decreasing meltblown layer weight at surfactant add-on rates of 0.2 and 0.3 liter/min. The strike-through time and rewet demonstrated by the SMS fabrics of Runs 1 and 2 are nearly the same as those for a carded web having a basis weight of 19.1 gsm, considering experimental/testing standard deviation as shown in Table 4. In addition, the CD strength of the SMS fabric has been improved significantly (1,000 gm/inch vs. 300 gm/inch) compared to the CD strength of the carded web. The CD strength is a major factor contributing to cut width stability at a slitting station. A statistical analysis of Table 4 indicates that the variability of the testing results, such as strike-through time and rewet, seems to have no obvious trend with respect to changes in melt-blown layer basis weights and surfactant add-on levels.

Based on the analysis of the experimental results above, the following conclusions can be drawn:

(1) The strike-through time and rewet demonstrated by the SMS laminate having a 1.8-gsm meltblown layer are nearly the same as for the carded web of 19.1 gsm, considering the experimental/testing standard deviation; and the CD strength, a major factor contributing to cutting length stability, of the SMS laminate with a 1.8-gsm meltblown layer has been improved significantly compared to the carded web (1,000 vs. 300 gm/inch).

(2) Decreasing the meltblown layer basis weight does not significantly improve the strike-through time at a surfactant add-on rate of 0.2 or 0.3 liter/min.

(3) Increasing the meltblown layer basis weight consistently decreases rewet with the exception of for the SS bilaminate at the surfactant add-on rate of 0.2 liter/min, and rewet decreases with a lower surfactant add-on rate.

(4) The strike-through time was consistently improved (decreased) with the higher surfactant add-on level, but not very significantly.

(5) Both CD and MD tensile strengths have no obvious correlation with either meltblown layer basis weight or surfactant add-on level.

(6) The air permeability consistently increases with decreasing meltblown layer basis weight at surfactant add-on rates of 0.2 and 0.3 liter/min.

In accordance with the preferred embodiments of the invention, the total liquid flow through the parabolic foam distribution channels is in the range of 2.0–4.0 liters/min. The flow of surfactant ("surfactant load") is preferably in the range of 0.1–0.6 liter/min. The flow of air into the foam generator is preferably in the range of 200–600 liters/min. The surfactant add-on level preferably lies in the range of 0.1–2.0%. The surfactant add-on level is equal to the wet pick-up (%)×concn. of surfactant×(surfactant load/water load).

The preferred embodiments of the invention have been disclosed for the purpose of illustration. Variations and modifications of the disclosed preferred embodiments which fall within the concept of this invention will be readily apparent to persons skilled in the art. For example, it will be apparent that additional nonwoven layers can be added to either the SMS or the SS fabric laminate, the rsulting laminate being treated with surfactant in accordance with the method of the present invention. Also, it will be apparent that the method of applying surfactant in zones, in accordance with the broad concept of the invention, can be applied to fabric laminates having nonwoven layers of fibers other than meltblown or spunbonded fibers. All such variations and modifications are intended to be encompassed by the claims set forth hereinafter.

What is claimed is:

1. A fiber laminate comprising a layer of melt-blown fibers sandwiched between first and second layers of spunbonded fibers, said layer of meltblown fibers and said first and second layers of spunbonded fibers each being treated with surfactant over a first region of said fiber laminate and being not treated with said surfactant over a second region of said fiber laminate.

2. The fiber laminate as defined in claim 1, wherein said fiber laminate has a third region not treated with surfactant, said first region lying between and contiguous with said second and third regions.

3. The fiber laminate as defined in claim 1, wherein said surfactant in said first region of said fiber laminate is a foam residue.

4. The fiber laminate as defined in claim 1, wherein said first region of said fiber laminate is treated with surfactant by foam application on both sides of said fiber laminate.

5. The fiber laminate as defined in claim 1, wherein said meltblown fibers and said spunbonded fibers are made of polypropylene.

6. The fiber laminate as defined in claim 1, further comprising a transition zone between said first and second regions having a width of 2 to 15 mm.

7. A fiber laminate comprising a first layer of spunbonded fibers bonded to a second layer of spunbonded fibers, each of said first and second layers of spunbonded fibers being treated with surfactant over a first region of said fiber laminate and being not treated with said surfactant over a second region of said fiber laminate.

8. The fiber laminate as defined in claim 7, wherein said fiber laminate has a third region not treated with surfactant, said first region lying between and contiguous with said second and third regions.

9. The fiber laminate as defined in claim 7, wherein said surfactant in said first region of said fiber laminate is a foam residue.

10. The fiber laminate as defined in claim 7, wherein said first region of said fiber laminate is treated with surfactant by foam application on both sides of said fiber laminate.

11. The fiber laminate as defined in claim 7, wherein said spunbonded fibers are made of polypropylene.

12. The fiber laminate as defined in claim 7, further comprising a transition zone between said first and second regions having a width of 2 to 15 mm.

13. A method of manufacturing a spunbonded/meltblown/spunbonded fiber laminate, comprising the steps of:

spinbonding a first nonwoven layer of fibers on a moving conveyor belt;

meltblowing a second nonwoven layer of fibers on top of said first nonwoven layer;

spinbonding a third nonwoven layer of fibers on top of said second nonwoven layer;

bonding said first, second and third layers together to form a spunbonded/meltblown/spunbonded fiber laminate; and treating both sides of said spunbonded/meltblown/spunbonded fiber laminate with surfactant over a first region while not treating said spunbonded/meltblown/spunbonded fiber laminate with surfactant over a second region.

14. The method as defined in claim 13, wherein said treating step comprises applying foam on both sides of said first region of said spunbonded/meltblown/spunbonded fiber laminate.

15. The method as defined in claim 14, further comprising the step of heating at least said first region of said spunbonded/meltblown/spunbonded fiber laminate.

16. A method of manufacturing a spunbonded/spunbonded fiber laminate, comprising the steps of:

a spinbonding a first nonwoven layer of fibers on a moving conveyor belt;

spinbonding a second nonwoven layer of fibers on top of said first nonwoven layer;

bonding said first and second layers together to form a spunbonded/spunbonded fiber laminate; and treating both sides of said spunbonded/spunbonded fiber laminate with surfactant over a first region while not treating said spunbonded/spunbonded fiber laminate with surfactant over a second region.

17. The method as defined in claim 16, wherein said treating step comprises applying foam on both sides of said first region of said spunbonded/spunbonded fiber laminate.

18. The method as defined in claim 17, further comprising the step of heating at least said first region of said spunbonded/spunbonded fiber laminate.

19. A method of manufacturing a nonwoven fiber laminate, comprising the steps of:

forming a first nonwoven layer of fibers;

forming a second nonwoven layer of fibers;

arranging said second nonwoven layer on said first nonwoven layer;

bonding said first and second nonwoven layers together to form a nonwoven fiber laminate; and applying surfactant on both sides of said nonwoven fiber laminate over a first region while not applying surfactant on either side of said nonwoven fiber laminate over a second region.

20. The method as defined in claim 19, wherein said applying step comprises applying foam on both sides of said first region of said nonwoven fiber laminate.

21. The method as defined in claim 19, wherein said steps of forming first and second nonwoven layers are performed by spinbonding.

22. A method of manufacturing a nonwoven fiber laminate, comprising the steps of:

forming a first nonwoven layer of fibers;

forming a second nonwoven layer of fibers;

forming a third nonwoven layer of fibers;

arranging said first, second and third nonwoven layers in a stacked relationship, said first nonwoven layer being sandwiched between said second and third nonwoven layers;

bonding said first, second and third nonwoven layers while in said stacked relationship to form a nonwoven fiber laminate; and applying surfactant on both sides of said nonwoven fiber laminate over a first region while not applying surfactant on either side of said non woven fiber laminate over a second region.

23. The method as defined in claim 22, wherein said applying step comprises applying foam on both sides of said first region of said nonwoven fiber laminate.

24. The method as defined in claim 22, wherein said steps of forming first and third nonwoven layers are performed by spinbonding, and said step of forming a second nonwoven layer is performed by meltblowing.

25. A fiber laminate comprising a first nonwoven layer of fibers bonded to a second nonwoven layer of fibers, said first and second nonwoven layers of fibers each being treated with surfactant over first and second regions of said fiber laminate and being not treated with said surfactant over a third region of said fiber laminate lying between said first and second regions, said first and second regions extending in parallel in a machine direction, said first region having a substantially constant first dimension in a cross direction perpendicular to said machine direction, and said second region having a substantially constant second dimension in said cross direction.

26. The fiber laminate as defined in claim 25, wherein said first nonwoven layer comprises a layer of meltblown fibers and said second nonwoven layer comprises a first layer of spunbonded fibers.

27. The fiber laminate as defined in claim 25, wherein said first nonwoven layer comprises a layer of spunbonded fibers and said second nonwoven layer comprises a layer of spunbonded fibers.

28. The fiber laminate as defined in claim 26, further comprising a second layer of spunbonded fibers, said layer of meltblown fibers being sandwiched between said first and second layers of spunbonded fibers, wherein said second layer of spunbonded fibers is treated with surfactant over said first and second regions of said fiber laminate and is not treated with said surfactant over said third region.

29. The fiber laminate as defined in claim 25, wherein said surfactant in said first and second regions of said fiber laminate is a foam residue.

30. The fiber laminate as defined in claim 25, wherein said first and second regions of said fiber laminate are treated with surfactant by foam application on both sides of said fiber laminate.

31. The fiber laminate as defined in claim 25, wherein said fibers of said first and second nonwoven layers are made of polypropylene.

32. The fiber laminate as defined in claim 25, further comprising a first transition zone between said first and third regions and a second transition zone between said second and third regions, each of said first and second transition zones having a width of 2 to 15 mm.

* * * * *

UNITED STATES PATENT AND TRADEMARK OFFICE
CERTIFICATE OF CORRECTION

PATENT NO : 6,139,941
DATED : Oct. 31, 2000
INVENTOR(S): Jankevics, Juris; Roberts, Glenn It is certified that error appears in the above-identified patent and that said Letters Patent is hereby corrected as shown below:

Table 3, Column: Run 6, Line: MD ELONG %: Replace "40" with -- 57 --.

Table 3, Column: Run 7, Line: MD ELONG %: Replace "55" with -- 40 --.

Table 3, Column: Run 8, Line: MD ELONG %: Replace "47" with -- 55 --.

Table 3, Column: Carded Web, Line: MD ELONG %: Insert -- 47 --.

Table 3, Column: Run 5, Line: CHEMICAL: Replace "0.291" with -- 0.201 --.

Claim 22, Column 16, Line 66: Replace "non woven" with -- nonwoven --.

Signed and Sealed this

Twenty-second Day of May, 2001

Attest:

NICHOLAS P. GODICI

Attesting Officer

Acting Director of the United States Patent and Trademark Office